May 14, 1940. J. I. DEARBORN Plant Pat. 397
VIOLET
Filed Sept. 26, 1939
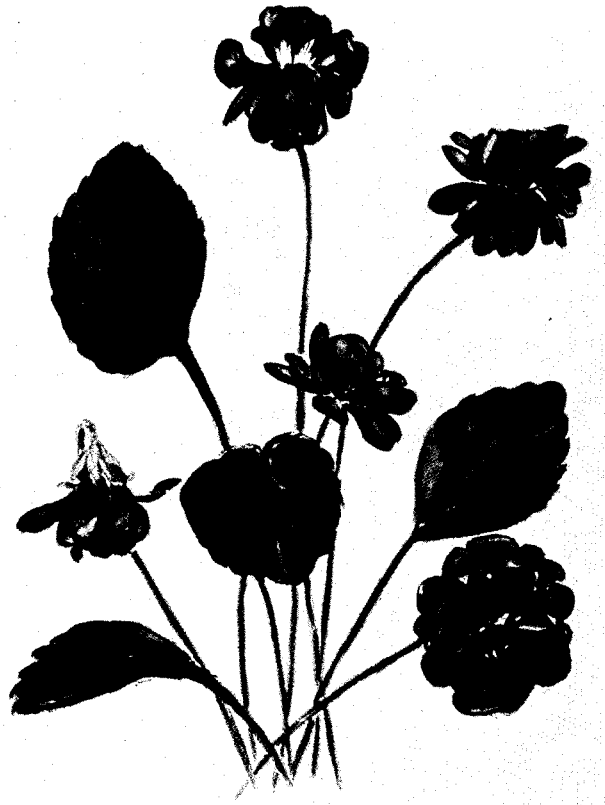
Julia Isabelle Dearborn.
Inventor
By Orville M. Kile
Plant Patent Agt.

Patented May 14, 1940

Plant Pat. 397

UNITED STATES PATENT OFFICE

397

VIOLET

Julia Isabelle Dearborn, Corvallis, Oreg.

Application September 26, 1939, Serial No. 296,675

1 Claim. (Cl. 47—60)

My new violet is of the double flowering, fragrant type and the known variety which it most resembles is the Double Russian. It differs greatly from that variety, however, particularly in the greater intensity of the color of its flowers and the firmer texture and smaller size of its leaves which grow in more compact form. Distinguishing qualities also to be noted in the new variety are the intense fragrance, extreme hardiness, prolific flowering and profuse production of runners.

My new variety originated as a chance seedling in my garden located in Lane County, Oregon. I had in my garden a fragrant purple single violet of an unknown variety. A great many bees and humming birds visit my garden during the summer and I assume that this new variety is a result of cross pollination between the single variety in my garden as the female parent and an unknown variety from which pollen was carried by the bees and humming birds. However, there is also a possibility that the variety resulted from self-pollination.

All reproduction of this variety has been by means of runners and division. Only a very few seeds have ever been produced and apparently they are not viable.

The plants and flowers resulting from the asexual reproduction of this new variety through several years, show no variation in their characteristics from the original seedling.

The original illustrations accompanying this application show several blossoms of this variety in various stages of opening, together with some of the stems and leaves. They are shown in approximately their true natural colors and size.

Following is a detailed description of my new violet plant. Color plate references indicate Ridgway's Color Standards and Nomenclature.

*The plant*

Growth: Vigorous; very hardy and prolific. Multiplies rapidly by means of many runners and stolons. Blossoms profusely.

Foliage: Plentiful.

*Leaves.*—Shape—broadly cordate; apex obtuse; basal lobes broad, generally remaining inrolled at maturity. Margins—broadly low crenate. Texture—thick; somewhat leathery when grown in the sun, softer if grown in shade. Appearance—velvety-pubescent, particularly below; prominently veined. Color—approximately Dusky Olive Green (Plate XLI). Size—up to 2¼ inches long by 2 inches wide.

*Petiole.* — Appearance — slender; erect; Broadly channelled; minutely pubescent. Strength—great. Size—small, averaging 3 inches in length. Color—slightly lighter than leaves.

*The Flower*

*Bud:* Color more intense than that of open flower, approximately Urania Blue (Plate XXIV) covered with a deep purple bloom.

Blossom: Both showy and cleistogamous flowers appear.

*Showy flowers.*—Borne singly on upright peduncles. Size—up to 1¼ inches in diameter. Shape—round in outline; very double. Fragrance—intense and very pleasing. Peduncle—strong; several shades lighter than leaf, approximately Lincoln Green (Plate XLI). Petals, arrangement—very double, with inner petals much smaller than outer ones. Size—outer petals ⅜ to ½ inch in length and slightly less in width. Shape—obovate to oval. Color—Urania Blue to Dusky Blue-Violet (Plate XXIV), with white markings at the base.

*Cleistogamous flowers.*—Low, inconspicuous.

Seeds: Rarely produced; apparently not viable.

Having thus disclosed my discovery, I claim:

A new and distinct variety of double violet characterized particularly by its firm-textured, broad, compact leaves; its intensely fragrant flowers of Urania Blue to Dusky Blue Violet; its vigor and hardiness; and its profuse production of runners and blossoms.

JULIA ISABELLE DEARBORN.